United States Patent [19]

Kita et al.

[11] 4,245,049
[45] Jan. 13, 1981

[54] PREPARATION OF 2-KETO-L-GULONIC ACID

[75] Inventors: Donald A. Kita, Essex, Conn.; Karlene E. Hall, Brooklyn, N.Y.

[73] Assignee: Pfizer Inc., New York, N.Y.

[21] Appl. No.: 113,945

[22] Filed: Jan. 21, 1980

[51] Int. Cl.$^3$ ............................................... C12P 7/60
[52] U.S. Cl. ................................................... 435/138
[58] Field of Search ........................................ 435/138

[56] References Cited

U.S. PATENT DOCUMENTS

| | | |
|---|---|---|
| 3,907,639 | 9/1975 | Makover ............................... 435/138 |
| 3,922,194 | 11/1975 | Sonoyama et al. ................... 435/138 |
| 3,959,076 | 5/1976 | Sonoyama et al. ................... 435/138 |
| 3,963,574 | 6/1976 | Sonoyama et al. ................... 435/138 |
| 3,998,697 | 12/1976 | Sonoyama et al. ................... 435/138 |

*Primary Examiner*—Alvin E. Tanenholtz
*Attorney, Agent, or Firm*—Francis X. Murphy; Charles J. Knuth; Peter C. Richardson

[57] ABSTRACT

2-Keto-L-gulonic acid, an ascorbic acid intermediate, is prepared by cultivating a microorganism of the genus Citrobacter in an aqueous nutrient medium in the presence of 2,5-diketo-D-gluconic acid.

8 Claims, No Drawings

PREPARATION OF 2-KETO-L-GULONIC ACID

BACKGROUND OF INVENTION

This invention relates to the preparation of 2-keto-L-gulonic acid by microbiological means.

2-keto-L-gulonic acid is a valuable intermediate in the preparation of ascorbic acid (vitamin C), an essential vitamin for human nutrition. Processes for converting 2-keto-L-gulonic acid to ascorbic acid, for example by heating in the presence of a base, are well known in the art.

Only a limited number of microorganisms are known in the art to be effective for the reduction of 2,5-diketo-D-gluconic acid to form 2-keto-L-gulonic acid, as shown for example in U.S. Pat. Nos. 3,963,574, 3,922,194 and 3,959,076. Microorganisms of the genus Citrobacter have not previously been disclosed to be effective in this reaction.

SUMMARY OF THE INVENTION

In accord with the present invention, it has now been discovered that a process for the preparation of 2-keto-L-gulonic acid or salts thereof in good yields is provided by cultivating a 2-keto-L-gulonic acid-producing microorganism of the genus Citrobacter or mutants thereof in an aqueous nutrient medium in the presence of 2,5-diketo-D-gluconic acid or a salt thereof. The fermentation is preferably conducted at a temperature of about 25° to about 35° C., most preferably at about 25° C. to 30° C. and at a pH in the range from about 5.5 to 7.5. Preferred 2,5-diketo-D-gluconic acid salts are sodium 2,5-diketo-D-gluconate and calcium 2,5-diketo-D-gluconate. The microorganisms include *Citrobacter freundii* and *Citrobacter diversus* and preferred strains of microorganism for use in this invention are *Citrobacter freundii* ATCC Nos. 6750 and 10787.

DETAILED DESCRIPTION OF INVENTION

The microorganisms useful in the present invention are 2-keto-L-gulonic acid-producing strains of the genus Citrobacter. A number of Citrobacter species are known and strains thereof are publicly available from culture collections, for example the American Type Culture Collection. For example, the American Type Culture Collection includes deposited strains of *Citrobacter freundii* designated as ATCC Nos. 8090, 6750, 8454, 10787, 11102, 11606, 11811 and 14135 and *Citrobacter diversus* designated as ATCC Nos. 27026, 27027, 27028 and 27156. As is noted in the American Culture Collection Catalogue (13th Edition), several deposited strains of *Citrobacter freundii* and *Citrobacter diversus* had earlier been classified as belonging to other genera or species. Thus, for example, *Citrobacter freundii* ATCC No. 6750 has also been described as *Citrobacter intermedium* and as *Escherichia intermedium*. For purposes of the present disclosure and claims such earlier classification is superceded by their identification as strains of *Citrobacter freundii* and *Citrobacter diversus*. Thus, the microorganisms useful in the present invention are those which meet the standard classification criteria for the genus Citrobacter, as described for example, in Bergy's Manual of Determinative Microbiology (8th Edition) (The William & Wilkins Company) and in the American Type Culture Catalogue (13th Edition) and the references cited therein. It is to be understood that for the production of 2-keto-L-gulonic acid according to the present invention, limitation to the aforesaid microorganisms is not intended. It is specifically intended to include mutants produced from these microorganisms by various means such as by irradiation with x-rays or ultraviolet light, treatment with nitrogen mustards, and the like, and such mutants are embraced by the specification and claims hereof. The 2-keto-L-gulonic acid producing capability of any strain of microorganism for the present invention can be readily determined by cultivating the microorganism in the presence of 2,5-diketo-D-gluconic acid or a salt thereof in an aqueous nutrient medium, in accord with the description and examples hereof.

The Citrobacter strain is cultivated in the presence of 2,5-diketo-D-gluconic acid or a salt thereof in an aqueous nutrient medium containing a carbon source, such as glucose, sorbitol, fructose, sucrose, glycerol or the like. Glucose, desirably in the form of glucose monohydrate (cerelose) is a preferred carbon source. It will be understood that, in accord with conventional fermentation practice, the nutrient medium will also contain sources of nitrogen, potassium, phosphorous and magnesium. The use of the term aqueous nutrient medium in the specification and claims hereof is meant to define a medium containing the nutrients described above, together with, if desired, any further sources of nutritional elements. The carbon source will generally be present in the nutrient medium at a concentration from about 0.5 to 15 grams per liter, preferably about 1 to 5 grams per liter. The nitrogen can be economically provided by the use of urea or inorganic nitrogen sources, such as ammonium sulphate, ammonium nitrate, ammonium phosphate or similar salts, each in concentrations from about 0.1 gram to 2 grams per liter of the nutrient medium. The potassium, magnesium and phosphorous are readily provided by the addition of salts such as potassium phosphate, ammonium phosphate, magnesium sulphate or similar salts, generally in amounts from about 0.1 gram to about 2 grams per liter of fermentation medium. The concentration of the above nutrients is not critical and considerable variation in the composition of the nutrient medium is possible. Other suitable media will be readily apparent to those skilled in the art and the present process is not intended to be limited to the use of the particular media described above and in the examples hereof.

In accord with conventional fermentation practice, the Citrobacter strain will generally be initially introduced into an aqueous inoculum medium containing nutrients as described herein above, and desirably containing additional nutrients such as yeast extract or peptone. The microorganism is then cultivated for a period of about 1 to 3 days, preferably at a temperature from about 25° C. to about 35° C., most preferably from about 25° to 30° C. and at a pH in the range about 5 to 7.5.

A suitable volume, for example about 1 to 10% (vol.-/vol.) of the resulting inoculum medium containing the Citrobacter strain is then introduced into the aqueous nutrient medium employed in the reduction of 2,5-diketo-D-gluconic acid. The 2,5-diketo-D-gluconic acid may be present in the aqueous nutrient medium when the inoculum is added or, preferably, may be introduced after a further period, for example after about 8 to 36 hours of incubation. The 2,5-diketo-D-gluconic acid may be added in the form of the free acid or as a salt thereof, for example as an alkali metal salt or an alkaline earth metal salt thereof. Preferred salts are sodium and calcium 2,5-diketo-D-gluconate. The 2,5-diketo-D-gluconic acid or salt may be produced by fermentation methods well known in the art; see, for example, U.S. Pat. No. 3,790,444. An aliquot of the 2,5-diketo-D-gluconic acid fermentation broth may be added to the aqueous nutrient solution containing the Citrobacter strain. Alternatively, the 2,5-diketo-D-gluconic acid or salt may be isolated from the fermentation broth and added to the Citrobacter containing nutrient medium. Preferably, the 2,5-diketo-D-gluconic acid starting material is added as an aliquot of the 2,5-diketo-D-gluconic acid-containing fermentation broth produced by the aerobic cultivation of *Acetobacter cerinus* in a glucose containing medium, as described in Belgian Pat. No. 872095 and in copending application Ser. No. 79,665, filed Sept. 28, 1979. Such a fermentation broth will contain from about 5 to about 20% (weight/vol.) of 2,5-diketo-D-gluconic acid, or a salt thereof, and a sufficient volume of broth should be added to the Citrobacter nutrient medium to provide an initial concentration of 2,5-diketo-D-gluconic acid or a salt thereof of about 1.0 to 10% (weight/vol.). Alternatively, isolated 2,5-diketo-D-gluconic acid or a salt thereof can be added to provide this concentration of 2,5-diketo-D-gluconic acid in the Citrobacter fermentation medium. The fermentation of the Citrobacter strain in the 2,5-diketo-D-gluconic acid-containing nutrient medium is conducted at a temperature of about 25° C. to about 35° C., preferably from about 25° C. to 30° C. During the fermentation the pH of the medium is preferably maintained in the range from about 5.5 to 7.5, by addition of an acid or base, as necessary. Suitable acids include sulfuric acid and phosphoric acid. Suitable bases include alkali metal hydroxides, preferably sodium hydroxide or alkali metal or alkaline earth metal carbonate, such as sodium carbonate or calcium carbonate. It will be understood that when such salts are added to the nutrient medium for pH control, the 2-keto-L-gulonic acid will be obtained in the form of the corresponding metal salt, for example the sodium or calcium salt, or mixtures thereof, and the production of such salts is embraced by the specifications and claims hereof. During the fermentation the mixture will be agitated, for example with a mechanical stirrer or by shaking the reaction vessel.

If desired, additional 2,5-diketo-D-gluconic acid or a salt thereof may be added to the medium during the course of the fermentation, after utilization of some of the initial 2,5-diketo-D-gluconic acid by the *Citrobacter freundii*, in order to obtain higher concentrations of the desired 2-keto-L-gulonic acid or salt in the reaction medium.

The *Citrobacter freundii* microorganism is cultivated until conversion to 2-keto-L-gulonic acid is substantially complete. For example, using *Citrobacter freundii* ATCC No. 6750, conversion of the 2,5-diketo-D-gluconic acid or salt will be substantially complete in about 36 to about 72 hours, depending on the initial concentration of 2,5-diketo-D-gluconic acid, the fermentation temperature and other conditions, and will provide 2-keto-L-gulonic acid in a yield of about 30% based on the 2,5-diketo-D-gluconic acid starting material. The progress of the fermentation reaction can be followed by determination of the concentration of 2,5-diketo-D-gluconic acid remaining in the reaction medium and the concentration of 2-keto-L-gulonic acid produced, using analytical methods well known to the art, including paper chromatography, thin layer chromatography and high pressure liquid chromatography. The identity of the product as 2-keto-L-gulonic acid may then be confirmed by isolation and characterization using conventional methods. See, for example J.C.S. Chem. Comm. 1979, 740.

The 2-keto-L-gulonic acid or salt thereof produced in the fermentation as described hereinabove can be isolated and purified by means known in the art. For example, the fermentation broth may be filtered and the 2-keto-L-gulonic acid, or its sodium or calcium salt, precipitated by the addition of a non-solvent such as a lower alkyl alcohol, especially methanol or ethanol. Other methods of isolation, such as removal of the solvent, for example by freeze drying, may also be employed.

When isolated in the form of a salt, the free 2-keto-L-gulonic acid may be obtained by addition of a mineral acid to a solution of salt, for example using sulfuric or hydrochloric acid, or by use of a cation-exchange resin. When the 2-keto-L-gulonic acid is isolated as the free acid, the corresponding salts are readily prepared by conventional means, such as by the reaction with an appropriate alkali metal hydroxide or carbonate or an alkaline earth metal carbonate.

The invention is illustrated by the following examples. However it should be understood that the invention is not limited to the specific details of these examples.

EXAMPLE 1

The following inoculum medium having a pH of 7.0, was prepared:

| Sorbitol | 3 g/l |
|---|---|
| Yeast Extract | 2 g/l |
| Peptone | 2 g/l |
| $KH_2PO_4$ | 1 g/l |
| $MgSO_4 \cdot 7H_2O$ | 0.2 g/l |

A 300 ml flask containing 100 ml of this inoculum medium was inoculated with cells of *Citrobacter freundii* ATCC No. 6750 from a nutrient agar slant (1 ml of a 10 ml. sterile aqueous suspension). The cells were cultivated for 24 hours at a temperature of 28° C. while the flask was on a rotary shaker. 100 ml of the following fermentation medium:

| Cerelose | 2 g/l |
|---|---|
| $(NH_4)_2HPO_4$ | 1 g/l |
| $KH_2PO_4$ | 1 g/l |
| $MgSO_4 \cdot 7H_2O$ | 0.5 g/l |
| Beet Molasses | 2 g/l |
| Glycine | 0.2 g/l | having a pH of 6.7 was placed in a 300 ml flask and inoculated with 5% v/v of the 24 hour inoculum culture described above and shaken for 22 hours on a rotary shaker, when the pH was approximately 5. 15 ml of fermentation broth containing 15–20% (wt/vol) sodium 2,5-diketo-D-gluconate and prepared by the fermentation of *Acetobacter cerinus* strain IFO 3263 in a glucose containing medium at 28° C. for 50 hours, was added to the *Citrobacter freundii* culture and the pH was adjusted to 6.5 by addition of sodium hydroxide. The fermentation was continued at 28° C., readjusting the pH to 6.5 every 24 hours. After 52 hours the 2,5-diketogluconate was essentially consumed, to give sodium 2-keto-L- gulonate in a yield of about 30%, based on the 2,5-diketo-D-gluconate starting material.

EXAMPLE 2

The procedure of Example 1 was repeated in a series of experiments using, instead of strain ATCC No. 6750, *Citrobacter freundii* ATCC Nos. 8090, 8454, 10787, 11102, 11606, 11811 and 14135 and *Citrobacter diversus* ATCC Nos. 27026, 27027, 27028 and 27156 and the formation of 2-keto-L-gulonic acid confirmed.

EXAMPLE 3

An inoculum medium as described in Example 1 was inoculated with cells of *Citrobacter freundii* ATCC No. 6750 (1 ml. of a 10 ml. sterile aqueous suspension) and the cells were cultivated for 20 hours at a temperature of 28° C.

1800 ml of the fermentation medium of Example 1 was placed in a 4 liter stirred pot and inoculated with 5% v/v of the 20 hour inoculum culture described above and cultivated for 8 hours at a temperature of 28° C. while stirring at 1750 r.p.m. with a propeller having a pitch of 0° and aerating the medium at 1 v/v/min. After the 8 hours of cultivation, 200 ml of fermentation broth containing 15–20% (wt/vol) sodium 2,5-diketo-D-gluconate, as described in Example 1, was added. The pH was adjusted to 6.5 by addition of sodium hydroxide and the aeration rate was reduced to 0.3 v/v/min. The fermentation was continued at 28° C., readjusting the pH to 6.5 every 24 hours. After 48 hours the 2,5-diketo-D-gluconate was essentially consumed to give sodium 2-keto-L-gulonate in a yield of about 25%, based on the 2,5-diketo-D-gluconate starting material.

We claim:

1. A process for producing 2-keto-L-gulonic acid or a salt thereof which comprises cultivating a 2-keto-L-gulonic acid-producing microorganism of the genus Citrobacter in an aqueous nutrient medium in the presence of 2,5-diketo-D-gluconic acid or a salt thereof.

2. A process according to claim 1 wherein the microorganism is a strain of *Citrobacter freundii* or *Citrobacter diversus*.

3. A process according to claim 1 wherein the 2,5-diketo-D-gluconic acid salt is sodium 2,5-diketo-D-gluconate.

4. A process according to claim 1 wherein the 2,5-diketo-D-gluconic acid salt is calcium 2,5-diketo-D-gluconate.

5. A process according to claim 1 wherein the cultivation is conducted at a pH of from about 5.5 to about 7.5.

6. A process according to claim 1 wherein the cultivation is conducted at a temperature of from about 25° C. to about 35° C.

7. A process according to claim 2 wherein said strain is *Citrobacter freundii* ATCC No. 6750.

8. A process according to claim 2 wherein said strain is *Citrobacter freundii* ATCC No. 10787.

* * * * *